United States Patent
Kopperschmidt et al.

(10) Patent No.: US 11,992,588 B2
(45) Date of Patent: May 28, 2024

(54) BLOOD HOSE SET, A CONTROL DEVICE OR CLOSED-LOOP CONTROL DEVICE, A BLOOD TREATMENT APPARATUS AND A METHOD FOR THE SINGLE-NEEDLE TREATMENT

(71) Applicant: Fresenius Medical Care Deutschland GmbH, Bad Homburg (DE)

(72) Inventors: Pascal Kopperschmidt, Dittelbrun (DE); Christian Schlaeper, Wehrheim (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 718 days.

(21) Appl. No.: 17/046,069

(22) PCT Filed: Apr. 8, 2019

(86) PCT No.: PCT/EP2019/058762
§ 371 (c)(1),
(2) Date: Oct. 8, 2020

(87) PCT Pub. No.: WO2019/197314
PCT Pub. Date: Oct. 17, 2019

(65) Prior Publication Data
US 2021/0030938 A1 Feb. 4, 2021

(30) Foreign Application Priority Data
Apr. 10, 2018 (DE) ..................... 10 2018 108 492.7

(51) Int. Cl.
*A61M 1/16* (2006.01)
*A61M 1/26* (2006.01)
(Continued)

(52) U.S. Cl.
CPC ............. *A61M 1/1601* (2014.02); *A61M 1/16* (2013.01); *A61M 1/267* (2014.02); *A61M 1/30* (2013.01);
(Continued)

(58) Field of Classification Search
CPC ...... A61M 1/16; A61M 1/1601; A61M 1/267; A61M 1/30; A61M 1/301; A61M 1/305;
(Continued)

(56) References Cited

U.S. PATENT DOCUMENTS

| 4,713,171 A | 12/1987 | Polaschegg |
| 5,047,147 A * | 9/1991 | Chevallet ................ A61M 1/30 |
| | | 210/101 |

(Continued)

FOREIGN PATENT DOCUMENTS

| DE | 216630 | 12/1984 |
| DE | 19917522 | 10/2000 |

(Continued)

OTHER PUBLICATIONS

PCT International Preliminary Report on Patentability in International Appln. No. PCT/EP2019/058762, dated Oct. 22, 2020, 19 pages (with English translation).

(Continued)

*Primary Examiner* — John Kim
(74) *Attorney, Agent, or Firm* — Fish & Richardson P.C.

(57) ABSTRACT

The present disclosure relates to a blood hose set, or to an extracorporeal blood circuit, for a single-needle treatment. In some embodiments, the set includes: a patient hose line and a Y-shaped connector or three-way connecter, which is connected to the patient hose line. In some embodiments, the blood hose set does not include any single-needle chamber in a blood path or on a blood side, nor is it connected to any single-needle chamber provided in a blood path or on a
(Continued)

blood side. The present disclosure further relates to a control device or closed-loop control device, a blood treatment apparatus, a method for the single-needle treatment, a digital storage medium, a computer program product and a computer program.

5 Claims, 4 Drawing Sheets

(51) Int. Cl.
| | | |
|---|---|---|
| *A61M 1/30* | (2006.01) | |
| *A61M 1/34* | (2006.01) | |
| *A61M 1/36* | (2006.01) | |
| *A61M 39/10* | (2006.01) | |
| *A61M 39/28* | (2006.01) | |

(52) U.S. Cl.
CPC ............ *A61M 1/301* (2014.02); *A61M 1/305* (2014.02); *A61M 1/34* (2013.01); *A61M 1/3413* (2013.01); *A61M 1/3427* (2014.02); *A61M 1/3434* (2014.02); *A61M 1/3622* (2022.05); *A61M 1/36224* (2022.05); *A61M 1/36225* (2022.05); *A61M 39/105* (2013.01); *A61M 39/28* (2013.01); *A61M 1/362262* (2022.05); *A61M 1/362265* (2022.05); *A61M 2205/12* (2013.01); *A61M 2205/3331* (2013.01)

(58) Field of Classification Search
CPC .... A61M 1/34; A61M 1/3413; A61M 1/3427; A61M 1/3434; A61M 1/3622; A61M 1/36224; A61M 1/36225; A61M 1/362262; A61M 1/362265; A61M 39/105; A61M 39/28; A61M 2205/12; A61M 2205/3331
See application file for complete search history.

(56) References Cited

U.S. PATENT DOCUMENTS

| | | |
|---|---|---|
| 5,120,303 A | 6/1992 | Hombrouckx |
| 2008/0015487 A1 | 1/2008 | Szamosfalvi et al. |
| 2010/0274168 A1 | 10/2010 | Gronau et al. |
| 2011/0178452 A1 | 7/2011 | Kopperschmidt |
| 2013/0079698 A1 | 3/2013 | Bocklet et al. |
| 2014/0213957 A1 | 7/2014 | Bocklet |

FOREIGN PATENT DOCUMENTS

| | | |
|---|---|---|
| EP | 0115835 | 8/1984 |
| EP | 0143064 | 5/1985 |
| EP | 3287159 | 2/2018 |
| FR | 2252106 | 6/1975 |
| WO | WO 89/03696 | 5/1989 |
| WO | WO 01/51106 | 7/2001 |
| WO | WO 01/89599 | 11/2001 |
| WO | WO 2009/006489 | 1/2009 |
| WO | WO 2009/127624 | 10/2009 |
| WO | WO 2010/121819 | 10/2010 |
| WO | WO 2011/151075 | 12/2011 |
| WO | WO 2012/004103 | 1/2012 |
| WO | WO 2014/118021 | 8/2014 |
| WO | WO 2015/173713 | 11/2015 |

OTHER PUBLICATIONS

PCT International Search Report and Written Opinion in International Appln. No. PCT/EP2019/058762, dated Jul. 12, 2019, 28 pages (with English translation).
Polaschegg et al., "Hemodialysis machines and monitors," Replacement of Renal Function by Dialysis, 5th ed., 2004, p. 365.

* cited by examiner

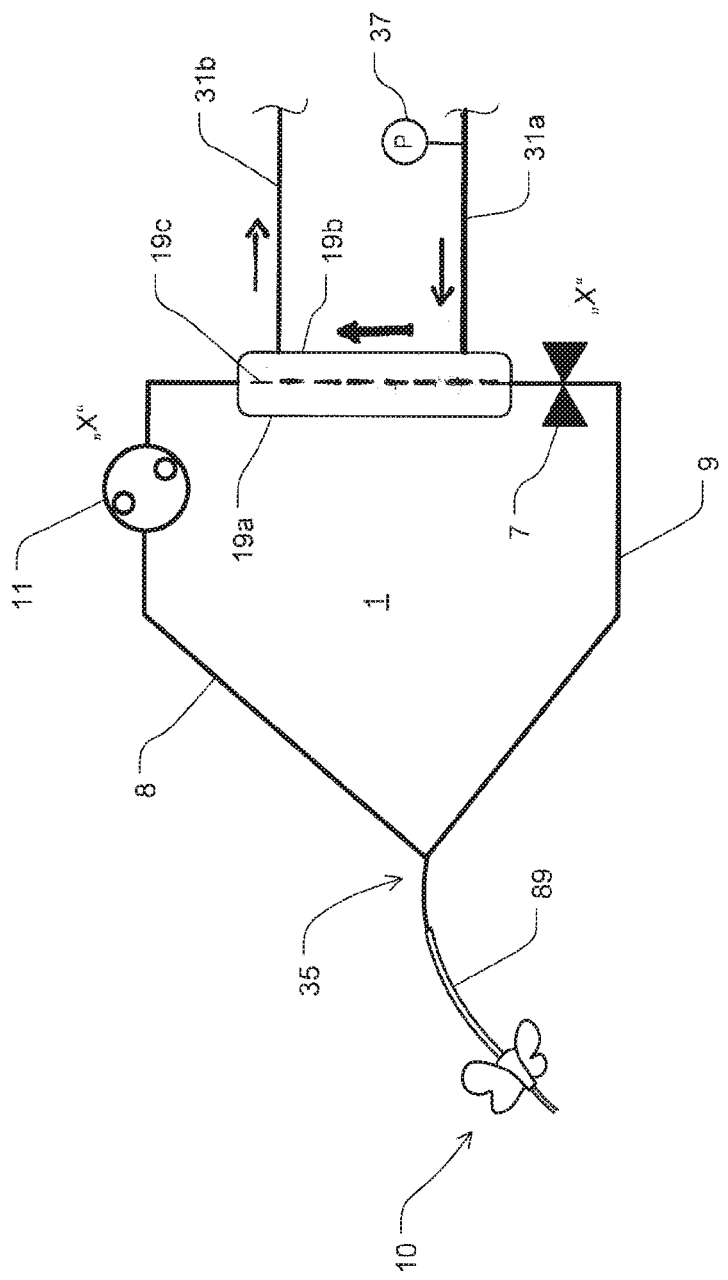

BLOOD HOSE SET, A CONTROL DEVICE OR CLOSED-LOOP CONTROL DEVICE, A BLOOD TREATMENT APPARATUS AND A METHOD FOR THE SINGLE-NEEDLE TREATMENT

CROSS-REFERENCE TO RELATED APPLICATIONS

The present application is the national stage entry of International Patent Application No. PCT/EP2019/058762, filed on Apr. 8, 2019, and claims priority to Application No. 10 2018 108 492.7, filed in the Federal Republic of Germany on Apr. 10, 2018, the disclosures of which are expressly incorporated herein in their entirety by reference thereto.

FIELD OF THE INVENTION

The present disclosure relates to a blood hose set and to a control or closed-loop control device (herein in short: control device) of a blood treatment apparatus. It further relates to a blood treatment apparatus as well as to a method for purifying blood. Furthermore, the present disclosure relates to using a blood hose set, also to a digital storage medium, a computer program product and a computer program.

Apparatuses for the extracorporeal treatment of blood are known from the field practice, with which blood is withdrawn from the patient via a vascular access with only one needle (e.g. the so-called single needle dialysis) for the extracorporeal blood treatment and returned back to the patient.

BACKGROUND

In single needle methods for the extracorporeal blood treatment, it is distinguished between a so-called arterial phase, in which blood is withdrawn from the patient via e.g. a cannula, and the so-called venous phase or return phase, in which blood is returned back to the vascular system of the patient via the same single cannula. Between these two phases, the blood is purified in a blood treatment device, usually a blood filter or dialyzer. In the known apparatuses and methods for the single-needle treatment, the blood is further stored—between these phases—in a buffer container which is arranged in the extracorporeal blood circuit (i.e. on the blood side) in order to allow switching between the two phases.

For the single needle method, it is significant or indicative to use only one cannula or one single lumen catheter, or generally speaking, only one vascular access device through which patient's blood is alternately conveyed, e.g. from one, in particular short, shunt to the dialysis device and conveyed back to the patient after being purified. The method is used especially in emergency situations.

The method of single-needle treatment is described in more detail, for example in DRUKKER, PARSONS and MAHER, 5th Edition, Kluwer Academic Publishers, Dordrecht, 2004, page 365.

SUMMARY

The present disclosure describes a further method for executing a single-needle treatment. In addition, a blood hose set, a control device and a blood treatment apparatus suitable for this purpose are described, which are suitable or configured to execute the method according to the present disclosure, as well as the use of the blood hose set according to the present disclosure. Furthermore, a suitable digital storage medium, a suitable computer program product and a suitable computer program for executing the method are described herein.

In all of the following statements, the use of the expression "may be" or "may have" and so on, is to be understood synonymously with "preferably is" or "preferably has," and so on respectively, and is intended to illustrate embodiments according to the present disclosure.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" as encompassing "at least one". This understanding is also equally encompassed by the present disclosure as the interpretation that a numeric word, for example, "one" may alternatively mean "exactly one", wherever this is evidently technically possible for the person skilled in the art. Both are encompassed by the present disclosure and apply herein to all used numerical words.

Whenever "programmed" or "configured" is mentioned herein, it is also disclosed that these terms are interchangeable.

The information "top" and "bottom" are herein to be understood in case of doubt by the person skilled in the art as absolute or relative spatial information, which refer to the orientation of the respective element when used as intended.

The blood hose set according to the present disclosure is suitable for a single-needle treatment.

It encompasses a patient hose line which is provided or arranged for both withdrawing blood from the patient blood circuit therethrough and introducing it into the patient blood hose as well as for withdrawing blood from the blood hose set and guiding it back into the patient blood circuit.

The blood hose set according to the present disclosure further encompasses a Y-shaped connector or a three-way connector. The connector is connected to the patient hose line.

In this, the blood hose set comprises however no single needle chamber provided on the blood side or is also not connected, in particular in fluid communication, to any single needle chamber provided on the blood side.

Whenever the term "blood side" is used herein, it thus refers to or designates those sections through which the blood to be treated flows or is pumped extracorporeally as intended during the blood treatment, or those which are connected to it, such as an arterial pressure gauge, an optical densitometer, etc. A blood hose set would therefore be assigned to the blood side (since blood flows through it during use), while lines by which dialysis liquid is conveyed to the blood filter or dialysate is conveyed away from the blood filter, as well as other sections of the blood treatment apparatus are referred to as the machine side or hydraulic side.

Whenever a single needle chamber is mentioned herein, this is to be understood as a storage device for temporarily storing blood or whole blood between one step of blood withdrawal through the patient hose line and the subsequent step of blood return through the patient hose line. An alternative term for single needle chamber is e.g. "compliance chamber". These terms may be herein interchangeable.

Whenever a single needle chamber is mentioned herein, this is not to be understood as a blood filter or a dialyzer having a mostly semipermeable membrane. Single needle chambers and blood filters or dialyzers are to be understood herein as different, separate components.

The blood hose set according to the present disclosure may be an extracorporeal blood circuit.

The control device according to the present disclosure is configured or designed for controlling or closed-loop controlling a blood treatment apparatus for treating blood by a single needle method.

The blood treatment apparatus comprises a blood pump, which is connectable to a—e.g. according to the present disclosure—blood hose set, e.g. as described supra. The pump is designed for conveying blood through the blood hose set, wherein said pump is operable in a withdrawal direction and preferably, in particular alternating, also in a return direction (i.e. for example backwards).

The blood treatment apparatus to be controlled comprises a return pump. The return pump may be for example the blood pump, which conveys e.g. in the opposite or counter direction in order to return blood. Alternatively or additionally, the return pump may be, or may comprise, a compressed air source, a hydraulic pump, dialysis liquid pump, substituate pump or any other pump. The return pump is optionally arranged to convey blood towards the blood hose set or a section thereof in a return direction during use of the blood treatment apparatus. Alternatively, the return pump is optionally connectable to the blood hose set according to the present disclosure or to a section thereof or is in fluid communication therewith in order to serve for conveying blood through the blood treatment apparatus and/or through the blood hose set in a return direction.

In this, in some embodiments the control device is configured or programmed to execute a method using the blood treatment apparatus, said method encompassing the following steps a) and b) repeatedly alternating:

a) the blood pump is operated in a withdrawal direction, in which blood is withdrawn from the patient blood circuit and pumped along a patient hose line into the blood hose set according to the present disclosure. Therefore, it withdraws blood from the patient in this step. The volume of the blood withdrawn in this step may be e.g. between 30 ml and 100 ml.

b) The return pump is operated in a return direction. Therethrough or thereby, blood is pumped out of the blood hose set and is hereby pumped along the patient hose line back into the patient blood circuit. The volume of the blood given back to the patient ("re-infused") in this step is between 30 ml and 100 ml. The volume should preferably correspond to the volume of blood withdrawn in step a) in order to achieve a balanced volume or mass balance. After completion of step b), a new cycle of steps a) and b) may be started by starting a further step a).

In this, the blood is not stored in a single needle chamber provided on the blood side between its withdrawal in step a) and its return in step b).

The blood treatment apparatus according to the present disclosure which is suitable to execute a single needle blood treatment comprises a blood pump which is connectable to a—e.g. according to the present disclosure—blood hose set, e.g. as described supra. The pump is designed to convey blood through the blood hose set, wherein it is operable in a withdrawal direction and preferably, e.g. alternating, also in a return direction.

The blood treatment apparatus comprises a return pump. The return pump may be e.g. the blood pump which conveys for the return phase e.g. in the opposite direction. Alternatively or additionally, the return pump may be a compressed air source, a hydraulic pump, dialysis liquid pump, substituate pump or any other pump. The return pump is optionally arranged so that it conveys fluid during use of the blood treatment apparatus in a return direction towards the blood hose set or a section thereof. Alternatively, the return pump is connectable to the blood hose set according to the present disclosure or to a section thereof or is designed to be in fluid communication therewith to serve for or to contribute to conveying blood through the blood hose set in a return direction.

Furthermore, in some embodiments the blood treatment apparatus according to the present disclosure comprises a control or closed-loop control device which is configured or programmed to control or closed-loop control the blood treatment apparatus. In this, the control device is configured or programmed to execute the method by using the blood treatment apparatus, said method encompassing the following steps a) and b), which may also be referred to as arterial phase or venous phase, alternating several times:

a) the blood pump is operated in a withdrawal direction, in which blood is withdrawn from the patient blood circuit and pumped along a patient hose line into the blood hose set according to the present disclosure. Therefore, it withdraws blood from the patient in this step. The volume of the blood withdrawn in this step may be e.g. between 30 ml and 100 ml.

b) The return pump is operated in a return direction. Therethrough or thereby, blood is pumped out of the blood hose set and pumped along the patient hose line back into the patient blood circuit. The volume of the blood given back to the patient ("re-infused") in this step is between 30 ml and 100 ml. The volume will correspond to the blood volume withdrawn in step a). A new cycle of withdrawal and return may follow.

In this, blood is not stored in a single needle chamber provided on the blood side between its withdrawal in step a) and its return in step b).

The method according to the present disclosure for the purification of blood by a single needle method is executed using a blood treatment apparatus according to the present disclosure in order to purify blood by a single needle method.

Using the blood hose set according to the present disclosure for the single-needle treatment, in particular within the context of a blood treatment method described herein, blood is not temporarily stored in a single needle chamber or a compliance chamber provided on the blood side, i.e. not in a single needle chamber or compliance chamber which is part of the blood hose set and/or which is provided on the blood side.

A digital, in particular non-volatile, storage medium according to the present disclosure, in particular in the form of a machine-readable carrier, in particular in the form of a floppy disk, CD, DVD or a USB stick or an EPROM, in particular with electronically or optically readable control signals, can interact with a programmable computer system such that the machine-induced steps of the method according to the present disclosure are prompted.

A computer program product according to the present disclosure comprises a program code volatile or saved on a machine-readable carrier or a signal wave for prompting the machine-induced steps of the method according to the present disclosure when the computer program product runs on a computer. A computer program product can according to the present disclosure be understood as, for example, a computer program which is stored on a carrier, an embedded system as a comprehensive system with a computer program (for example, an electronic device with a computer program), a network of computer-implemented computer programs (for example, a client-server system, a cloud computing system, etc.) or a computer on which a computer program is loaded, running, saved, executed or developed.

The term "machine-readable carrier", as used herein, denotes in certain embodiments according to the present disclosure a carrier containing data or information, which is interpretable by software and/or hardware. The carrier may be a data carrier such as a floppy disk, a CD, DVD, a USB stick, a flashcard, an SD card or the like.

A computer program according to the present disclosure comprises a program code for prompting the machine-induced steps of the method according to the present disclosure, when the computer program runs on a computer. According to the present disclosure, a computer program can be understood as, for example, a physical, ready-for-distribution software product, which comprises a program.

It is applicable for the digital storage medium according to the present disclosure, the computer program product according to the present disclosure and the computer program according to the present disclosure that all, several or some of the machine-induced steps of the method according to the present disclosure are prompted. This applies particularly in interaction with a detecting device and/or with a blood treatment apparatus according to the present disclosure as described herein.

Embodiments according to the present disclosure may comprise one or several of the features mentioned above or in the following. In this, the features mentioned herein may, in any arbitrary combination, be subject-matter of embodiments according to the present disclosure, unless the person skilled in the art recognizes a specific combination as technically impossible.

Whenever an embodiment is mentioned herein, it is then an exemplary embodiment according to the present disclosure.

In some embodiments, blood is not temporarily stored in a single-needle chamber on the machine side or in a compliance chamber on the machine side, i.e. not in a single-needle chamber or compliance chamber, which is part of the hydraulic system and or is provided on the hydraulic side.

In several embodiments, the blood hose set comprises no further patient hose line in addition to a patient hose line which would be connected to the vascular circuit of the patient and/or to an access device but rather comprises only one in total.

In some embodiments, the blood hose set comprises exactly one access device for establishing an access between the patient hose line and the patient blood circuit.

An access device may for example be a needle, a connector etc. and is preferably single-lumen.

In some embodiments, the membrane may have a high membrane permeability (high flux).

In several embodiments, the method according to the present disclosure encompasses, as the method executed by the control device also does, optionally also closing a clamp or hose clamp disposed venously, i.e. downstream of the blood treatment device (blood filter, dialyzer, etc.), or a different kind of stopping of the blood flow downstream of the blood treatment device, during or prior to conveying blood in the above-mentioned step a) from the patient towards the blood filter.

Further, using the control device effects the transfer of volume, like e.g. plasma or blood water of the conveyed blood, through the semipermeable membrane of the blood filter by establishing a pressure difference, e.g. a pressure gradient, between the blood chamber and the dialysis liquid chamber. This may be achieved or supported by e.g. an active ultrafiltration on the hydraulic side using one or several ultrafiltration pumps and/or in a passive manner by volume shifting while reducing the pressure increase generated by the blood pump in the blood filter.

Finally, the method executed by the control device encompasses in several embodiments the opening of the venous hose clamp or the termination or clearing of the different kind of stopping.

Alternatively or additionally, the method or the method executed by the control device encompasses effecting the transfer of liquid from the dialysis liquid chamber through the semipermeable membrane into the blood chamber of the blood filter. This may e.g. be carried out by reducing a suitable pressure on the hydraulic side or the dialysis liquid side (dialysis side), while blood is pumped back into the patient blood circuit along the patient hose line in the above-mentioned step b).

In some embodiments, an optional addition of substituate liquid through a substituate addition site of the blood hose set, e.g. via a connector and e.g. from a substituate source takes place for example in this step instead of or in addition to returning fluid through the membrane. This may serve for or support the displacement of blood and the return of blood to the patient. A volume shifting in step b) through the membrane of the blood filter may therefore be omitted or supplemented in these embodiments In several embodiments, the method encompasses controlling and/or monitoring the method by analyzing pressure measurement values, in particular of the arterial and/or venous pressure sensor, and/or the motor current consumption of at least one of the pumps mentioned herein.

In some embodiments, step a) is ended, for which either the withdrawal activity of the blood pump is stopped or reduced or (alternatively or additionally) the return activity of the return pump is started or increased if, for example, the transmembrane pressure has reached or exceeded a value predetermined for the phase of step a). This value may be higher than other values which have been pre-set as limits for transmembrane pressure during other phases of the blood treatment. If the value predetermined for step a) has been reached/exceeded, a maximum desired or permissible hemoconcentration of the blood in the blood chamber of the blood filter is considered to have been reached. The apparatuses according to the present disclosure may be configured to perform or prompt this performance as also any other embodiment disclosed herewith.

In several embodiments, the method comprises a phase inserted or included between step a) (e.g. its end) and step b) (e.g. its start), referred to herein as the interim phase or step c). During this phase, the blood pump and optionally the return pump may be stopped or significantly slowed down. During this interim phase, the venous hose clamp may optionally be closed. The blood present in the blood chamber may be forced to remain in the blood chamber. During this interim phase, dialysis liquid may flow through the dialysis liquid chamber of the blood filter. The time period during which rinsing is carried out in this way may be for example more than 1 second, in particular between 1 and 30 seconds. The time during which rinsing is carried out in this may be limited to (or correspond to) the time it takes for a predetermined volume of dialysis liquid to flow through the dialysis liquid chamber of the blood filter. This volume may be set, for example, at 1-3 times the volume of the dialysis liquid chamber.

Inserting or providing such an interim phase may increase the efficiency of the blood purification, since during this phase fresh dialysis liquid is led past concentrated blood, separated by the semi-permeable membrane. It is the exploitation of the state of high concentration during the interim phase that leads to the increased diffusive limitation of the blood of uremic toxins by means of filtration and thus to the above-mentioned increase in efficiency.

In some embodiments, the interim phase described above is not strictly inserted between the withdrawal phase and the return phase such that either the withdrawal phase, the interim phase or the return phase would take place. Although this is exactly the case in some embodiments, but in other embodiments two of the aforementioned phases always overlap, i.e. either the withdrawal phase with the interim phase (which may then probably no longer be referred to as "interim"), or the interim phase with the return phase.

The interim phase may optionally no longer be present, but is accompanied by withdrawal flows or return flows for its entire duration.

The interim phase may optionally no longer be present on its own, but is accompanied by withdrawal flows or return flows throughout its entire duration.

Thus, in several embodiments, it may be provided that already during the phase of withdrawal referred to herein as step a), the pumps provided on the hydraulic side of the blood treatment apparatus (one located upstream of the dialysis liquid chamber of the blood filter, the other downstream of this chamber) may be used both to create a lower pressure or negative pressure (relative to the blood chamber) in the dialysis liquid chamber and to simultaneously maintain a dialysis liquid flow through the dialysis liquid chamber. In this way, both filtration and dialysis, i.e. blood purification may be performed in step a) both by convection and diffusion.

In several embodiments, the control device is configured to control or regulate the aforementioned pumps as described above, depending on the control of the blood pump, the return pump and/or valves or clamps such as the venous hose clamp. Thus, it may for example be programmed or configured to start the dialysis liquid flow along the semi-permeable membrane (without passing through it) after the effected transfer of plasma water across the semi-permeable membrane has been completed, for example because the blood pump is stopped or the venous tube clamp is opened or has been opened. It may also be configured to stop the flow of dialysis liquid along the membrane as soon as the fresh dialysis liquid or substituate or other liquid for infusion into the patient via the membrane is to be started on the blood side.

In several embodiments, the blood treatment apparatus is designed as a hemodialysis apparatus, a hemofiltration apparatus or a hemodiafiltration apparatus, in particular as an apparatus for the chronic renal replacement therapy or for the continuous renal replacement therapy (CRRT).

The blood treatment apparatus may be designed as an apparatus for the acute treatment, and dialysis liquid may be provided by e.g. a bag.

The blood treatment apparatus may be designed as an apparatus for the continuous treatment or for the treatment of patients who need permanent dialysis, and dialysis liquid may be mixed online e.g. by the treatment apparatus.

In several embodiments, the blood pump is also the return pump. The blood pump may be operated alternately in a withdrawal direction and in a return direction. Alternatively or additionally, the opening and closing of fluid paths within the blood hose set may cause the blood being sometimes removed from the patient and sometimes returned to the patient even when only one pump, e.g. the blood pump, is operated.

In several embodiments, no single needle chamber or compliance chamber is provided, not even on the hydraulic side. In particular, no single-needle chamber or compliance chamber, which is provided as an oscillation volume or volume for receiving and subsequently dispensing fluid between the dialysis liquid chamber and a waste pump or an ultrafiltration pump and connected to, or branches off, a line between the dialysis liquid chamber and a waste pump or an ultrafiltration pump, in particular via a branch line.

A compliance chamber is not understood here to be a volume that results or is created when elastic fluid lines, such as the arterial blood line or the venous blood line, expand beyond their nominal or resting volume when the internal line pressure is increased and can therefore take up more volume than before. Although this effect is usually also referred to as "compliance" (of the lines), the latter only describes a behavior of the material of the already existing line. However, a "compliance chamber", as this term is used here, is not this material behavior. A "compliance chamber" would rather be a chamber which is recognizable as such and which optionally has no other function than the intermediate storage of fluid. It may be in fluid communication with a line, e.g. it may be fluidically integrated in this line it may be connected to this line via a branch line. A compliance chamber is, however, optionally designed to be recognizable as such and/or differs from the line feeding it. If the compliance chamber would be imagined away, the line feeding it would optionally remain.

In several embodiments, the blood treatment apparatus comprises a conveying pump for conveying fresh dialysis liquid in the direction of the dialysis liquid chamber and a waste pump for conveying used dialysate in the direction away from the dialysis liquid chamber.

In several embodiments, the single needle chamber or the compliance chamber is provided. Unlike in the prior art, it is provided on the hydraulic side and not on the blood side.

Some or all of the embodiments according to the present disclosure may comprise one, several or all of the aforementioned and/or following advantages.

In conventional, completely air-free extracorporeal blood hose systems, there is no possibility to temporarily store the patient's blood during the a.m. phase change (transition between withdrawal and return). Although it is possible to implement the single needle method in such systems through connectable or dis-connectable single needle chamber, this requires, however, a complex set up or course for the phase-synchronized provision of a storage volume that meets the requirements. The required control of the blood treatment apparatus is thus comparatively complex. Furthermore, the required blood hose system may be significantly more complex than e.g. in the double needle method, in which blood is continuously withdrawn or returned via two vascular accesses. With the aid of the present disclosure described herein, it is advantageously possible to omit the complex set up for the phase-synchronized provision of the storage volume as well as the complex blood hose set.

Nevertheless, blood purification may advantageously take place by combining a diffusive and convective substance exchange.

Since the extracorporeal blood hose system may remain completely air free, blood/air contacts and the associated risk of coagulation are advantageously reduced or even avoided. Blood/air contacts as well as stagnations of the blood flow lead to an increased tendency for thrombosis in the blood hose system, which requires the increased use of anticoagulants. The safety of the patient in treatment is thus increased by the present disclosure. In addition, anticoagulants may advantageously be saved and/or their use reduced.

Another advantage is that no further actuator in the extracorporeal blood circuit is required in addition to the usual pumps, like e.g. the blood pump or the ultrafiltration pump. The method may therefore be implemented in existing device systems with little efforts.

BRIEF DESCRIPTION OF THE DRAWINGS

The present disclosure is exemplarily explained below with regard to the accompanying drawings in which identical reference numerals refer to the same or similar components. The following applies in the figures:

FIG. 2c shows in graphic representation an example of the schematic structure of the blood hose set according to the present disclosure of FIGS. 2a and 2b during an optional intermediate or interim phase.

DETAILED DESCRIPTION

Figure 1:
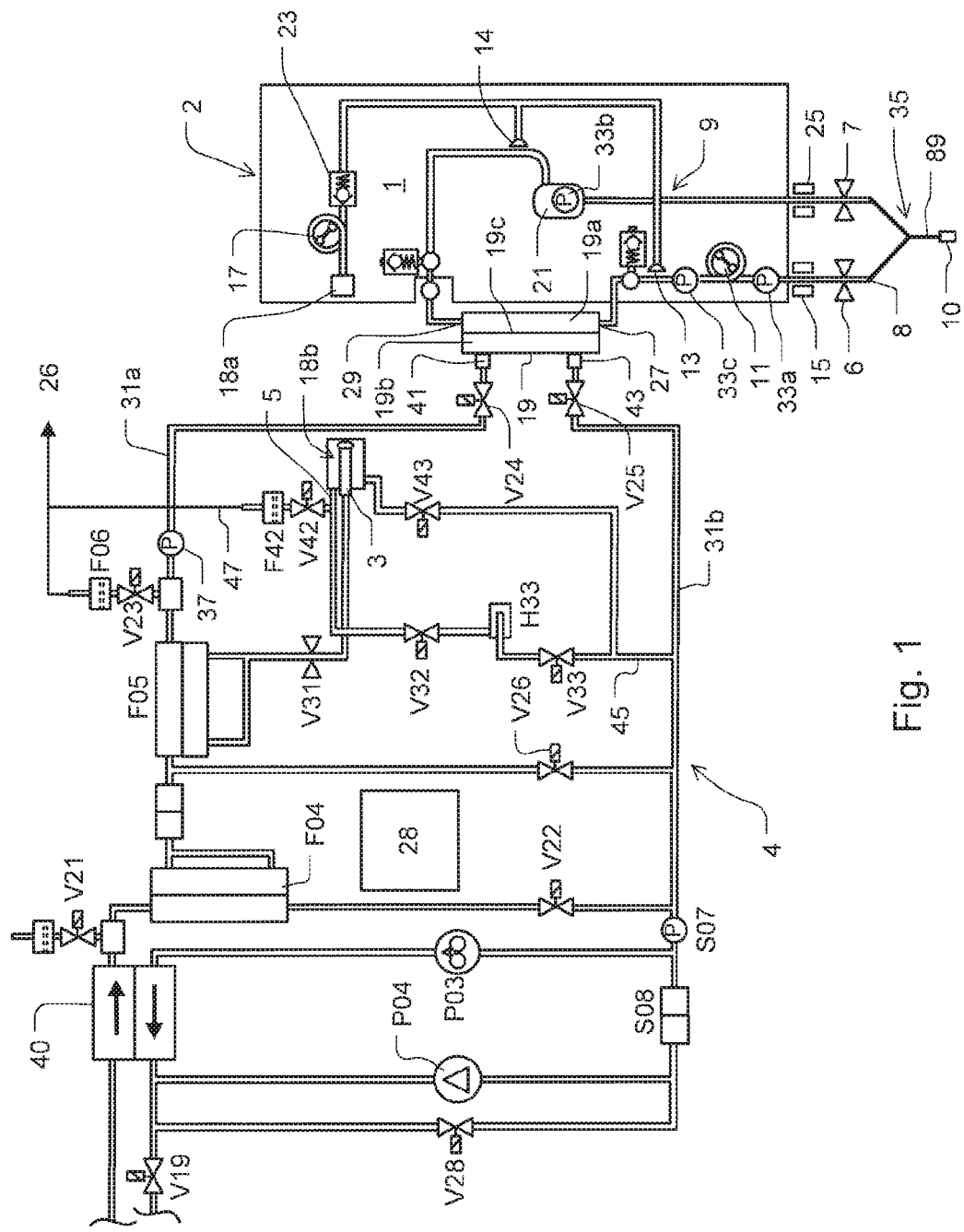
FIG. 1 shows a simplified illustration of a blood treatment apparatus according to the present disclosure with an extracorporeal blood circuit in a first embodiment.

FIG. 1 shows a simplified illustration of an exemplary embodiment of a blood treatment apparatus 4 according to the present disclosure 4, being connected to a blood hose set according to the present disclosure or and extracorporeal blood circuit 1. The blood treatment apparatus 4 of FIG. 1 is an apparatus for treating patients who need permanent or continuous dialysis. The blood treatment apparatus 4 is however not limited thereto.

The extracorporeal blood circuit 1 extends purely exemplarily outside and inside of a blood cassette 2 and connects the latter to the treatment apparatus 4 in fluid communication. The extracorporeal blood circuit 1 comprises exactly one access device 10, for example a connection needle, or is connected thereto. A fluid flow through the extracorporeal blood circuit 1 or through sections thereof may be prevented by an arterial hose clamp 6 arranged in its arterial blood line 8, further by a venous hose clamp 7 arranged it its venous blood line 9.

A section of the extracorporeal blood circuit 1 is inserted into a blood pump 11 of the blood treatment apparatus 4. The extracorporeal blood circuit 1 optionally comprises an addition site 13 for substituate liquid (in pre-dilution) and optionally an addition site 14 for substituate liquid (in post-dilution). The addition sites 13 and 14 are herein exemplarily designed as phantom valves. Phantom valves of such type are described in the application WO 2010/121819 A1 of the applicant of this present disclosure as well. For details, reference is made to that disclosure.

An optional arterial air-blood detector 15 is optionally provided on the arterial blood line 8.

FIG. 1 further shows a substituate pump 17 of the blood treatment apparatus 4. The substituate pump lies downstream of a connecting point, on which the blood cassette 2 may, prior to being used, be optionally connected via its substituate port 18a to an optional automatic substituate connector 18b of the blood treatment apparatus 4. In the example of FIG. 1, the automatic substituate connector 18b optionally comprises a first fluid guide 3, a second fluid guide 5 and a third fluid guide for rinsing the automatic substituate connector 18b and for conducting the substituate through the automatic substituate connector 18b.

A blood filter 19 having a blood chamber 19a and a dialysis liquid chamber 19b is arranged in the extracorporeal blood circuit 1. Blood chamber 19a and dialysis liquid chamber 19b are separated from each other by a semipermeable membrane 19c.

The blood cassette 2 optionally comprises a venous air-separation chamber 21.

A substituate line of the blood cassette 2 optionally comprises a check valve 23.

The extracorporeal blood circuit 1 optionally comprises a venous air-substituate liquid-blood detector 25 at the venous blood line 9.

The blood treatment apparatus 4 optionally comprises a compressed air source 26 or is connected thereto.

Further seen in FIG. 1 are a dialysis liquid inlet line 31a, which carries dialysis liquid into the dialysis liquid chamber 19b, and a dialysate outlet line 31b, which carries dialysate away from the dialysis liquid chamber 19b.

A pressure sensor 33a is optionally provided upstream of the blood pump 11 in the arterial blood line 8.

A pressure sensor 33b is optionally provided in the area of the venous air-separation chamber 21 in the venous blood line 9.

The pressure sensor 33c, also referred to as prefilter pressure sensor, is optionally provided downstream of the blood pump 11 in the arterial blood line 8. Said pressure sensor 33c may be arranged upstream of the addition site 13.

An again further pressure sensor 37 is optionally arranged in or at the dialysis liquid inlet line 31a between the pressure source 26 and the blood filter 19.

Valves V19, V22, V24, V25, V26, V28, V31, V32 and V33 are optional and provided in sections of the hydraulic system of the blood treatment apparatus 4.

The valve V24 is arranged in or at the dialysis liquid inlet line 31a.

The valve V25 is arranged in or at the dialysate outlet line 31b.

The valve V28 is arranged in a dialysate outlet line 31b.

The valve V31 is arranged in the first fluid guide 3 of the automatic substituate connector 18b or in a line leading towards it.

The valve V32 is arranged in the second fluid guide 5 of the automatic substituate connector 18b or in a line leading thereto.

The valve V33 is disposed in the drainage line 45.

The valve V19 is disposed downstream of all the abovementioned valves V24, V25, V28, V31, V32 and V33.

Further shown is an ultrafiltration pump P03. A hydraulic balance chamber 40 is only indicated.

A control or closed-loop control device 28 for the control or the closed-loop control of the blood treatment apparatus 4 is provided and may be in signal and/or control communication with all the a.m. components of the blood treatment apparatus 4.

In the prior art, during a single-needle treatment the patient blood conveyed extracorporeally is usually, before and after its purification, temporarily parked in a compliance chamber of the extracorporeal hose system, in order to render possible the alternating conveyance. In the first of the two alternating phases, the patient blood is conveyed through the one access via the blood pump 11 into the compliance chamber provided in a blood path or on a blood side, wherein the purifying process is not yet completed or is already completed. In the second phase the blood is pumped from the compliance chamber (usually by a further actuator or pump in addition to the blood pump 11) back to the patient. The volume of the compliance chamber corresponds to single needle stroke volume of the and is generally between 25 and 100 ml, occasionally between 30 and 60 ml. Such a conventional compliance chamber provided in a blood path or on the blood side of the extracorporeal hose system or blood hose set is not required or provided by the present disclosure.

FIG. 1 does not show the optional embodiment, likewise according to the present disclosure, by which a single-needle chamber or compliance chamber is provided on the hydraulic side, as part of the hydraulic or on the side of the blood treatment apparatus 4 (i.e. not in the blood hose set 1 or not physically connected thereto. Such a single-needle chamber or compliance chamber would be provided on the left side of the blood filter 19 with reference to FIG. 1, anyhow on the left side of the semipermeable membrane 19c, with respect to the illustration of FIG. 1.

Figure 2A:
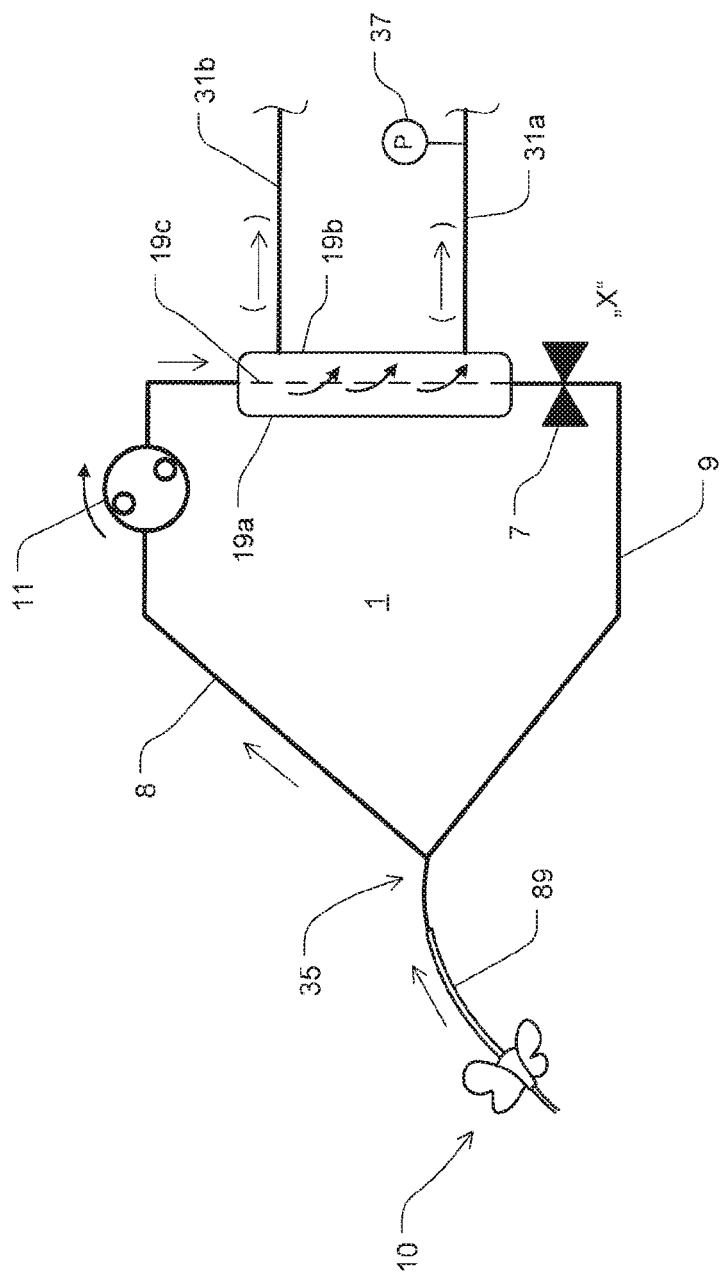
FIG. 2a shows an exemplary graphic illustration of the schematic structure of a blood hose set according to the present disclosure when in use during a withdrawal phase.

FIG. 2a shows an exemplary graphic illustration of the schematic structure of the blood hose set 1 according to the present disclosure during the first phase of the method according to the present disclosure designated above with a).

The method described with reference to FIG. 2a uses the volume of the dialysis liquid chamber 19b and possibly the lines of the hydraulic system of the blood treatment apparatus 4 connected to it to receive liquid portions of blood, preferably followed by their discarding in a sink, in a bag or the like. The connected lines may be the dialysis liquid inlet line 31a and/or the dialysate outlet line 31b.

According to the present disclosure, no whole blood is pumped through the semi-permeable membrane 19c into the hydraulic system and discarded via it, rather plasma water. This may be discarded as effluent or filtrate (e.g. into the basin or sink). During the transfer of plasma water to the hydraulic side, which takes place in the first phase (referred to above as step a)), the blood is hemoconcentrated in the blood chamber 19a of the blood filter 19. The plasma water is displaced or moved via the semipermeable membrane 19c of the blood filter 19, in that an increased pressure is built up in the blood chamber 19a by the blood pump 11 pumping towards the blood filter 19 with closed venous hose clamp 7. This pressure is higher than that prevailing in the dialysis liquid chamber 19b, i.e. on the dialysis liquid side of the blood filter 19. The resulting liquid flows or streams are indicated by arrows across the membrane 19c. They are further indicated by arrows, placed in parentheses, at the lines 31a and 31b. The parentheses are meant to imply that there may optionally be one or more flows, which arrows are in parentheses, it is however not mandatory.

The blood pump 11 obviously or clearly conveys so that there are flows also in the access device 89 and in the arterial blood line 8 towards the blood filter 19. In this, the venous hose clamp 7 is closed, which is indicated with an "X" next to the hose clamp 7. There is no blood flowing in the venous blood line 9, which is connected to the blood filter 19 downstream, because of the closed hose clamp 7.

Corpuscular components which cannot pass through the semipermeable membrane 19c, remain on the blood side of the blood filter 19, i.e. on the side of the blood chamber 19a, which leads to the a.m. concentration therein.

It can be seen that the blood hose set 1 according to the present disclosure used in FIG. 2a comprises no single needle chamber on the blood side. It is however connected to a blood filter 19 and used for the single-needle treatment.

The transfer of fluid via the semipermeable membrane 19c, i.e. from the blood chamber 19a into the dialysis liquid chamber 19b, taking place in the phase shown in FIG. 2a may be referred to as "positive ultrafiltration". The latter may be accompanied by an accepted balance deficiency or lack of balance at lease phased. The balance deficiency may for example be due to fluid from the hydraulic side or dialysis side (i.e. on the right of the semipermeable membrane 19c in FIG. 2a) which is discarded, e.g. in a sink/drain, e.g. via the drainage line 45 shown in FIG. 1.

Figure 2B:
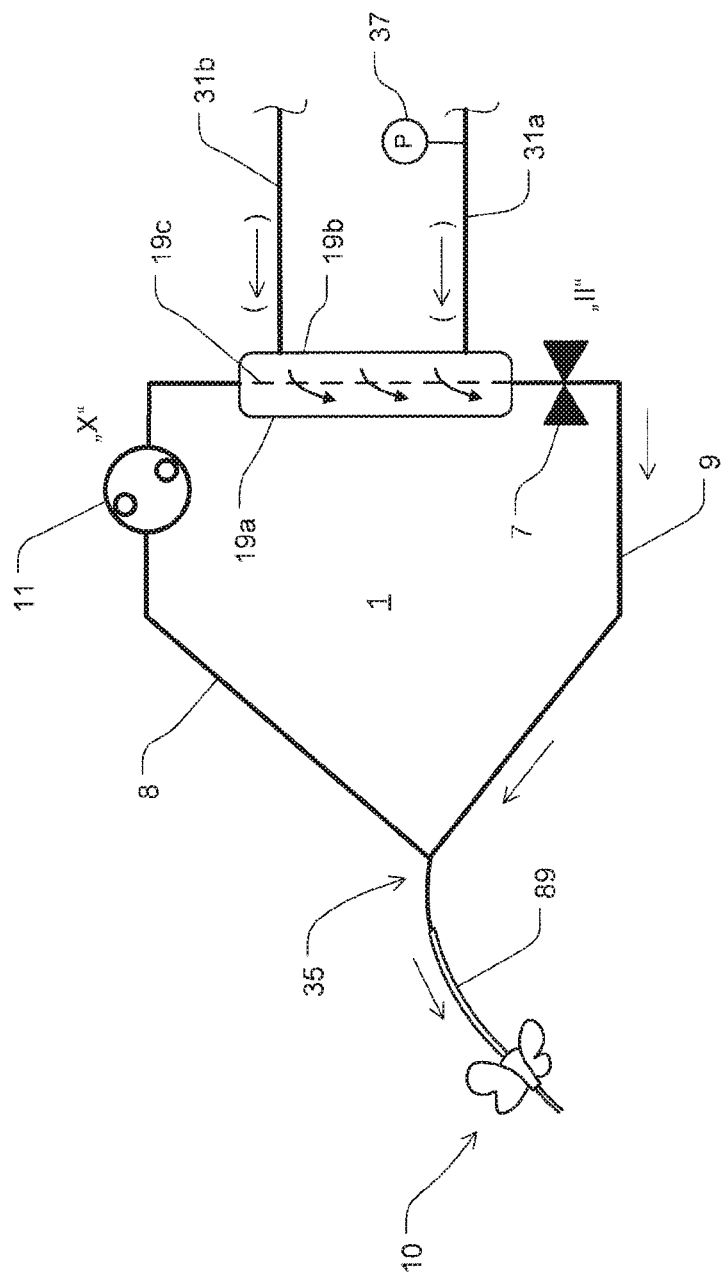
FIG. 2b shows an exemplary graphic illustration of the schematic structure of the blood hose set according to the present disclosure of FIG. 2a during a return phase.

FIG. 2b shows the blood hose set 1 according to the present disclosure shown in the illustration of FIG. 2a during the second phase of the method according to the present disclosure.

In the second phase (referred to above as step b)), a volume of liquid that optionally corresponds quantitatively to the volume of liquid previously displaced over the semipermeable membrane 19c is pressed over the semi-permeable membrane 19c and into the blood hose set 1. The liquid displaced in step b) is mostly fresh dialysis liquid or substituate solution, which comes for example from a bag or is produced by the blood treatment apparatus. The volume on the blood side of the blood filter 19 is optionally approx. 100-150 ml.

The flow conditions are essentially reversed in step b), measured by the conditions described in FIG. 2a.

In this, the blood pump 11 may be halted. If it is, as optionally shown in the figures, an occlusion pump, it then prevents a return flow of blood into the arterial blood line 8 in its idle state. In this, it does not increase the pressure downstream of the blood pump 11 due to its idle state.

Instead of or in addition to a possible occlusion effect of the blood pump 11, an arterial hose clamp (not shown in FIGS. 2a and 2b) may be provided in the arterial blood line 8. In the phase illustrated in FIG. 2b, it may prevent a flow of blood along the arterial blood line 8 away from the blood filter 19 and towards the patient. The arterial hose clamp may be the one with the reference numeral 6 in FIG. 1. It may be a hose clamp different therefrom and/or arranged at another position in the arterial blood line 8.

The pumping effect which leads to the transfer of fluid via or across the semipermeable membrane 19c, being indicated in FIG. 2b, may be caused by the ultrafiltration pump P03, not shown in FIG. 2b, or by any other pump on the dialysis side or hydraulic side, e.g. by a dialysis liquid pump.

FIG. 2c shows in the representation of FIGS. 2a and 2b, by way of example, the blood hose set 1 according to the present disclosure during the optional third phase of the method according to the present disclosure being provided between the first and the second phase.

In the third phase or interim phase (referred to above as step c)) no or essentially no volume of liquid is shifted across the semi-permeable membrane 19c. Rather, in step c), liquid, usually fresh dialysis liquid or substituate solution, for example from a bag or generated by the blood treatment apparatus, is passed along the semi-permeable membrane 19c through the dialysis liquid chamber 19b.

The blood pump 11 may stand still. If, as optionally shown in the figures, it is an occlusion pump, it prevents a return flow of blood into the arterial blood line 8 in its idle state.

Instead of or in addition to a possible occlusion effect of the blood pump 11, an arterial hose clamp (not shown in FIGS. 2a, 2b and 2c) may be provided in the arterial blood line 8. In the phase shown in FIG. 2c, it may prevent blood from flowing along the arterial blood line 8 in a direction away from the blood filter 19 and towards the patient. The arterial hose clamp may be the one with reference numeral 6 in FIG. 1. Deviating therefrom, it may be a different clamp and/or arranged elsewhere in the arterial blood line 8.

The resulting liquid flows are indicated by arrows along the membrane 19c. They are also indicated by arrows on the lines 31a and 31b.

As stated above, the blood pump 11 does not convey in this third phase (interim phase), so that there are no flows in the access device 89 and in the arterial blood line 8 in the direction of the blood filter 19. The venous hose clamp 7 is closed, which in turn is indicated by an "X" next to the hose clamp 7. In the venous blood line 9, which is connected downstream to the blood filter 19, there is no blood flowing either due to the closed hose clamp 7.

In this interim phase, corpuscular components that cannot overcome the semi-permeable membrane 19c remain on the blood side of the blood filter 19, i.e. on the side of blood chamber 19a. However, due to the osmotic pressure between blood chamber 19a and dialysis liquid chamber 19b, which is further increased by the above-mentioned hemoconcentration of uremic toxins, diffusion of membrane-permeable substances does nevertheless occur.

The transfer taking place in the phase shown in FIG. 2c solely by diffusion over the semi-permeable membrane 19c, i.e. from the blood chamber 19a into the dialysis liquid chamber 19b, may be referred to as "dialysis" or "hemodialysis".

The pumping effect which leads to the flow of fluid along but not across the semi-permeable membrane 19c as indicated in FIG. 2c may be effected by the ultrafiltration pump P03, not shown in FIG. 2c, or by any other pump on the dialysis side or hydraulic side (such as a two-chamber dosing pump which chambers alternately hold the chamber volume for filtration or substitution according to the above-mentioned phases), for example by a dialysis liquid pump.

A combination of the aforementioned steps a) and c) or b) and c) is not shown by the figures. For such combinations, the flows shown in FIGS. 2a and 2c or 2b and 2c by arrows may be respectively present together.

The following statements or elaborations explain more specific, exemplary designs or embodiments of the method according to the present disclosure.

According to the inventors, the blood volume in the blood filter 19 may be concentrated up to 33% (f=0.33). Thus, with a blood filter volume $V_{DB}$ of e.g. 120 ml, the maximum possible stroke volume $V_s$ calculated:

$$V_S = V_{DB} \cdot \frac{f}{1-f} = 120 \text{ ml} \cdot \frac{0.33}{1-0.33} = 60 \text{ ml} \quad (1)$$

Proof of the equation 1 (in analogy to the geometric series):

A volume $f^* V_{DB}$ displaced from the blood chamber 19a is, again, preferable by fresh substituate solution, returned to the blood circuit 1. Subsequently, a volume $f^* f^* V_{DB}$ is displaced and optionally discarded, which is again filled or replaced by fresh liquid (i.e. liquid, which did not yet come into contact with blood) and so on:

$$V_S = V_{DB} \cdot (f + f^2 + f^3 + \ldots) = f \cdot V_{DB} \cdot \sum_{n=0} f^n \quad (2)$$

Transformations for the a.m. term:

$$\sum_{n=0} f^n = \frac{1}{1-f}, f < 1 \quad (3)$$

and for the stroke volume $V_s$:

$$V_S = f \cdot V_{DB} \cdot \sum_{n=0} f^n = V_{DB} \cdot \frac{f}{1-f} \quad (4)$$

In detail, the following two repetitive method steps 1) and 2) are necessary for treating with the single needle therapy:

1) Patient's blood is conveyed into the blood filter 19 by the blood pump with closed venous hose clamp 7 (FIG. 2a), while in the present example approx. 33% of the blood volume is concentrated in the blood filter 19 by filtering off plasma water via or across the semipermeable membrane 19c into the hydraulic part.

The filtering off takes place either by active ultrafiltration provided on the hydraulic side, e.g. by the ultrafiltration pump P03 or without using pumps on the hydraulic side (dialysis side) by volume displacement during the decrease of increase in pressure generated by the blood pump 11 in the blood chamber 19a of the blood filter 19.

The maximum volume $V_s$ (stroke volume) to be displaced depends on the size of the volume $V_{DB}$ of the blood chamber 19a of the blood filter 19 provided on the blood side and on the concentration f and is calculated according to:

$$V_S = V_{DB} \cdot \frac{f}{1-f} \quad (5)$$

The hemoconcentration in the blood filter 19 leads to a decrease of the permeability of the semipermeable membrane 19c, which leads to an increase of the pressure in the blood chamber 19a. This may be measured by a pressure sensor between blood pump 11 and blood filter 19, e.g., the prefilter pressure sensor 33c, or may be estimated based on the electrical power consumption of the blood pump 11. The measured pressure, wherever measured, may be used to regulate the method according to the present disclosure, the apparatuses according to the present disclosure may be correspondingly configured. The pressure may additionally or alternatively, in particular when the venous hose clamp 7 is closed, be measured also at the venous pressure sensor 33b downstream of the blood filter 19.

The analysis of the pressure pulses generated by the peristaltic blood pump 11, which may be measured e.g. by the pressure sensor 37 on the hydraulic side, offers a further possibility for a feedback. As the membrane permeability decreases, the received pressure signal at the hydraulic pressure sensor 37 decreases.

2) Upon reaching the predetermined pressure value in the blood chamber 19a, the blood pump 11 is stopped and the venous hose clamp 7 is opened, while the volume is pumped back via the semipermeable membrane 19c into the blood hose set 1 due to overpressure in the hydraulic part.

The regained volume flows back towards the patient along the venous blood line 9. The volumes transported via the semipermeable membrane 19c are optionally balanced. The purification effect is caused in the blood filter 19 on the one hand by diffusive transport processes in the presence of dialysis liquid flow or dialysate flow and on the other hand by the convective transport of the plasma water to be displaced.

The stroke volumes desired to be achieved according to equation (1) are comparable to typical volumes in standard single needle therapies.

The transfer of fluid via the semipermeable membrane 19c, i.e. from the dialysis liquid chamber 19b into the blood chamber 19a, taking place in the phase shown in FIG. 2b may be referred to as "negative ultrafiltration". It may contribute to compensate the phase of the fluidic imbalance shown in FIG. 2a, which is in some embodiments at least phase-wise accepted, e.g. by the addition of substituate on the hydraulic side. The fluidic imbalance, which may have resulted e.g. due to fluid which has been discarded from the hydraulic side or dialysis side (i.e. to the right of semipermeable membrane 19c in FIG. 2a), may hereby be corrected or compensated.

The fluidic imbalance which occurs in the phase shown in FIG. 2a and which is compensated in the phase shown in FIG. 2b may be deliberately targeted and optionally predetermined in its amount.

LIST OF REFERENCE NUMERALS 1 extracorporeal blood circuit, blood hose set
2 blood cassette
3 first fluid guide of the automatic substituate connector 18b
4 blood treatment apparatus
5 second fluid guide of the automatic substituate connector 18b
6 arterial hose clamp
7 venous hose clamp
8 arterial blood line
9 venous blood line
10 inlet device
11 blood pump
13 addition site for substituate liquid (predilution)
14 addition site for substituate liquid (post dilution)
15 arterial air-blood-detector
17 substituate pump
18a automatic substituate port
18b automatic substituate connector
19 blood filter
19a blood chamber
19b dialysis liquid chamber
19c semipermeable membrane
21 venous air separation chamber
23 check valve of the substituate canal
25 venous air-blood detector or air-substituate liquid-blood detector
26 compressed air source
28 control device, control device and/or closed-loop control device
31a dialysis liquid inlet line
31b dialysate outlet line
33a, b pressure sensors
33c prefilter pressure sensor
35 Y-shaped connector
37 pressure sensor
40 hydraulic balance chamber
45 drainage line
89 patient hose line
V19 valve of dialysate outlet line 31b
V22 valve
V24 valve of dialysis liquid inlet line 31a
V25 valve of dialysate outlet line 31b
V26 valve
V28 valve of dialysate outlet line 31b
V31 valve of the first fluid guide 3 of the automatic substituate connector 18b
V32 valve of the second fluid guide 5 of the automatic substituate connector 18b
V33 first valve of the drainage line 45
P03 ultrafiltration pump

The invention claimed is:

1. A control device for control or closed-loop control of a blood treatment apparatus for treatment of blood by a single-needle method, wherein the blood treatment apparatus to be controlled or closed-loop controlled comprises:
  a blood pump connectable to a blood hose set for conveying blood through the blood hose set, wherein the blood pump is operable in a withdrawal direction;
  a return pump, arranged to convey fluid towards the blood hose set or to a section thereof and/or towards a patient in a return direction during use of the blood treatment apparatus;
  wherein the control device is configured to execute a method by using the blood treatment apparatus, the method encompassing the following steps:
    a) operating the blood pump in a withdrawal direction in which blood is withdrawn from a patient blood circuit and pumped along a patient hose line into the blood hose set; and
    b) operating the return pump such that blood is pumped out of the blood hose set and pumped back along the patient hose line into the patient blood circuit;
  wherein:
    steps a) and b) are executed several times alternately;
    blood is not stored in a single-needle chamber provided in a blood path or on a blood side between its withdrawal in step a) and its return in step b); and
    the method executed by the control device is controlled and/or monitored by or based on an analysis of pressure measurement values and/or by or based on a motor current or an electricity consumption of at least one pump.

2. The control device according to claim 1, wherein the method further encompasses:
  closing a venous hose clamp during or prior to conveying blood in step a) from the patient towards a blood filter;
  effecting transfer of plasma water of the conveyed blood via a semipermeable membrane of the blood filter by establishing a pressure difference between a dialysis liquid chamber and a blood chamber;
  opening the venous hose clamp; and
  effecting the transfer of liquid from the dialysis liquid chamber via the semipermeable membrane into the blood chamber of the blood filter by establishing a suitable pressure on a hydraulic side, while in step b) blood is being pumped back into the patient blood circuit along the patient hose line.

3. The control device according to claim 1, wherein the blood hose set comprises:
  the patient hose line for both blood withdrawal from the patient blood circuit into the blood hose set and for blood return from the blood hose set back into the patient blood circuit; and
  a Y-shaped connector or three-way connector which is connected to the patient hose line,
  wherein the blood hose set comprises in the blood path or on the blood side no single-needle chamber nor is the blood hose set connected to any single-needle chamber provided in the blood path or on the blood side.

4. A blood treatment apparatus for executing a single needle blood treatment, wherein the blood treatment apparatus comprises:
  a blood pump connectable to a blood hose set for conveying blood through the blood hose set, wherein the blood pump is operable in a withdrawal direction;
  a return pump, arranged to convey blood towards the blood hose set or to a section thereof and/or towards a patient in a return direction during use of the blood treatment apparatus;
  a control device configured to control or closed loop control the blood treatment apparatus;
  wherein:
    the control device is programmed to execute the single needle blood treatment by a method encompassing the following steps:
      a) operating the blood pump in a withdrawal direction in which blood is withdrawn from a patient blood circuit and pumped into the blood hose set; and
      b) operating the return pump such that the blood is pumped out of the blood hose set and pumped back into the patient blood circuit;
    wherein the steps a) and b) are executed several times alternately;
    blood is not intermediately stored in a single needle chamber provided in a blood path or on a blood side between its withdrawal in step a) and its return in step b); and
    the method executed by the control device is controlled and/or monitored by or based on an analysis of pressure measurement values and/or by or based on a motor current or an electricity consumption of at least one pump.

5. The blood treatment apparatus according to claim 4, wherein the blood treatment apparatus is embodied as a hemodialysis apparatus, a hemofiltration apparatus, a hemodiafiltration apparatus, an apparatus for chronic renal replacement therapy, or an apparatus for continuous renal replacement therapy (CRRT).

* * * * *